(12) United States Patent
Smith

(10) Patent No.: US 9,353,092 B2
(45) Date of Patent: May 31, 2016

(54) SYNTHESIS AND USE OF CROCONAINE COMPOUNDS

(71) Applicant: University of Notre Dame du Lac, Notre Dame, IN (US)

(72) Inventor: Bradley Smith, Granger, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 14/311,267

(22) Filed: Jun. 21, 2014

(65) Prior Publication Data

US 2015/0005501 A1     Jan. 1, 2015

Related U.S. Application Data

(60) Provisional application No. 61/840,252, filed on Jun. 27, 2013.

(51) Int. Cl.
    *C07D 409/14*      (2006.01)
    *C07D 409/08*      (2006.01)

(52) U.S. Cl.
    CPC ............ *C07D 409/14* (2013.01); *C07D 409/08* (2013.01)

(58) Field of Classification Search
    CPC ............................ C07D 409/14; C07D 409/08
    USPC .......................................... 546/187; 549/59
    See application file for complete search history.

(56) References Cited

U.S. PATENT DOCUMENTS

| | | |
|---|---|---|
| 6,258,340 B1 | 7/2001 | Licha et al. |
| 6,942,925 B1 | 9/2005 | Lazarev et al. |
| 6,944,493 B2 | 9/2005 | Alam et al. |
| 8,267,982 B2 | 9/2012 | Biel |
| 8,323,694 B2 | 12/2012 | Hainfeld |

FOREIGN PATENT DOCUMENTS

| | | | |
|---|---|---|---|
| DE | 294961 | * | 10/1983 |
| DE | 294961 | | 10/1991 |
| EP | 1014119 A1 | | 6/2000 |
| WO | 9104073 A1 | | 3/1991 |
| WO | 9708692 A1 | | 3/1997 |
| WO | WO9708692 | * | 3/1997 |
| WO | 03079339 A1 | | 9/2003 |
| WO | 2011018513 A1 | | 2/2011 |

OTHER PUBLICATIONS

Hartmann et al. "Preparation of Thieophene . . . " CA116:108305 (1992).*

(Continued)

*Primary Examiner* — Celia Chang
(74) *Attorney, Agent, or Firm* — Haukaas Fortius PLLC; Michael H. Haukaas

(57) ABSTRACT

The present disclosure provides compositions and methods for the synthesis and use of croconaine compounds. The disclosed compounds are easily prepared from croconic acid. A halothiophene is reacted with an alkanolamine, the resulting aminothiophene is modified by appending a desired functional group to the hydroxyl group, and the modified aminothiophene is reacted with croconic acid to form the final compound. Applications of such croconaine compounds include photothermal imaging, photothermal therapy, light-activated drug release, and tissue welding.

20 Claims, 12 Drawing Sheets

(56) References Cited

OTHER PUBLICATIONS

Song et al. "A New Water . . . " Dyes and Pigments 78 p. 60-64 (2008).*
The USPTO connection, p. 1-2 (2005).*
King "Medicinal Chemistry:Principle and Practice" p. 206-209 (1994).*
Avirah, R.R. et al., "Infrared Absorbing Crocaine Dyes: Synthesis and Metal Ion Binding Properties", J. Org. Chem. 2008, 73, 274-279.

Keil, D. et al., "Synthesis and Spectroscopic Characterization of New NIR Absorbing (2-Thienyl)-and (4-Dialkylaminoaryl)-Substituted Croconic Acid Dyes", Liebigs Annalen der Chemie, 1993, pp. 935-939.
Song, X. et al., "A New Water-Soluble Near-Infrared Croconium Dye", Dyes and Pigments 78 (2008) 60-64.
Yasui, S., "Syntheses and Some Properties of Infrared-Absorbing Croconium and Related Dyes", Dyes and Pigments 10 (1988), 13-22.

* cited by examiner

*FIG. 7*

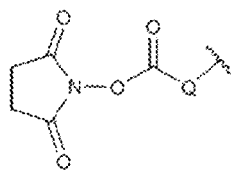
alkyl hydroxy succinimide ester

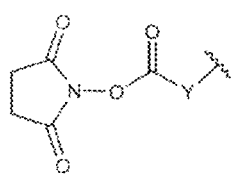
aryl hydroxy succinimide ester

1,2,4-triazole

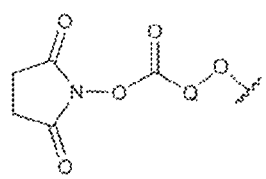
alkyloxy hydroxy succinimide ester

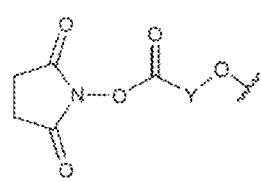
aryloxy hydroxy succinimide ester

1,2,3-triazole

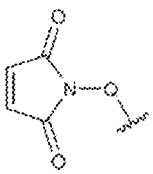
alkyl maleimide

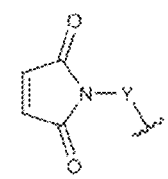
aryl maleimide

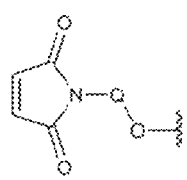
alkoky maleimide

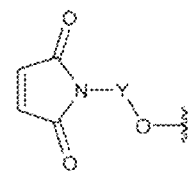
alkyloxy maleimide

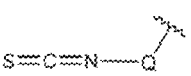
alkyl isothiocyanate

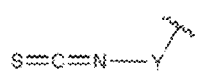
aryl isothiocyanate

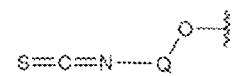
alkoxy isothiocyanate

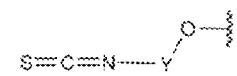
aryloxy isothiocyanate

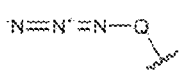
alkyl azide

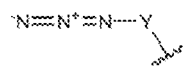
aryl azide

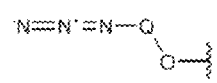
alkoxy azide

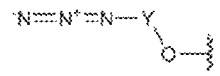
aryloxy azide

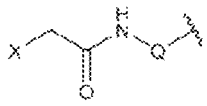
alkyl halo acetamido

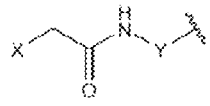
aryl halo acetamido

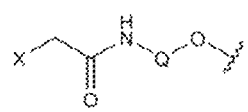
alkoxy halo acetamido

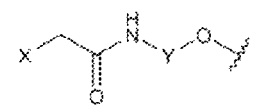
aryloxy halo acetamido

SYNTHESIS AND USE OF CROCONAINE COMPOUNDS

CROSS-REFERENCE TO RELATED APPLICATIONS

This application claims the benefit of the filing dates of U.S. provisional patent application Ser. No. 61/840,252, filed on Jun. 27, 2013, entitled "High Performance Near Infrared Photothermal Dyes," the disclosure of which is incorporated herein by reference.

STATEMENT REGARDING FEDERALLY SPONSORED RESEARCH OR DEVELOPMENT

This invention was made with government support under Grant No. CHE 1058699 awarded by the National Science Foundation. The government has certain rights in the invention.

BACKGROUND

1. Field

This disclosure relates to a croconaine compound and a method for making the same.

2. Background

Photodynamic therapy (PDT) is a form of light therapy, sometimes called phototherapy, using nontoxic light-sensitive compounds which become toxic when exposed to particular wavelengths of light, thereby disrupting the function of malignant or other diseased cells. PDT requires three key components: a photosensitive compound, a light source, and tissue molecular oxygen. When the compound is irradiated, it excites neighboring tissue oxygen to create reactive oxygen species which, in turn, react with surrounding tissue and disrupt various cell functions. A limitation of this method is that it is often not useful in hypoxic tissue. Additionally, many organic compounds are subject to photobleaching as well as degradation from interaction with the produced reactive oxygen species.

Photothermal therapy (PT) offers a related, but simpler and more widely applicable, method of phototherapy utilizing photothermal heating. Photothermal heating occurs when light energy is absorbed by the compound and released by non-radiative means. There is significant technical advantage to using non-ionizing, near-infrared light, especially light with wavelengths that are close to 800 nm, as it is less harmful to healthy living tissue and is capable of deep tissue penetration, which facilitates many procedures based on photothermal heating. Gold nanoparticles or nanorods are the best-known absorbing systems for PTT; however their large size, slow rates of diffusion, propensity to melt, potential for toxic buildup, and relative synthetic inflexibility limit their application. Current near-infrared absorbing organic compounds, although perhaps otherwise suitable, suffer from photobleaching, inefficient conversion of light into heat, and a propensity to produce reactive oxygen species. Although the latter feature is useful for PDT it is not useful in many photothermal applications such as drug release. For the aforementioned reasons, there is a need for biologically compatible, chemically stable, and synthetically flexible compounds which upon laser irradiation in the wavelength 750-850 nm provide efficient photothermal heating with very low production of reactive oxygen species and very low photobleaching.

SUMMARY

An object of the present disclosure is to provide at least one croconaine compound that can overcome the aforementioned photothermal heating limitations. These compounds have the formula (I):

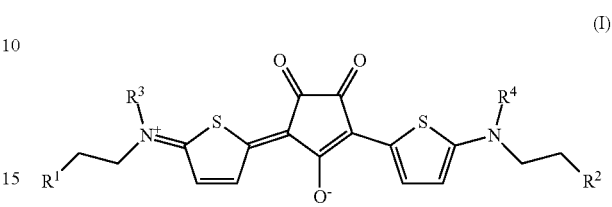

wherein $R^1$ and $R^2$ are each independently selected from the group consisting of —H, alkyl, substituted alkyl, arylalkyl, aryl, substituted aryl, heteroaryl, substituted heteroaryl, carboxylic acid, alkoxy, aryloxy, polyethylene glycol, amino, dialkylamino, halogen, triazole, amido, N-alkylamido, sulfone, sulfonate, phosphonate, and a first reactive group, $R^3$ and $R^4$ are each independently selected from the group consisting of —H, alkyl, substituted alkyl, arylalkyl, aryl, substituted aryl, heteroaryl, substituted heteroaryl, carboxylic acid, and a second reactive group, or wherein $R^1$ and $R^3$ taken together form an optionally substituted 5- or 6-membered ring, or wherein $R^2$ and $R^4$ taken together form an optionally substituted 5- or 6-membered ring, or a pharmaceutically acceptable salt, optical isomer, geometric isomer or tautomers thereof.

Such croconaine compounds absorb radiation and produce localized heating. This feature is useful in a number of applications including, but not limited to, thermal imaging, photothermal therapy, light-activated drug release, and tissue welding.

It is also an object of the present disclosure to provide a method for making at least one croconaine compound which provides photothermal heating in the 750-850 nm light wavelength range. The compound has a small size, high rate of diffusion, high thermal stability, high synthetic flexibility, high photostability and, upon irradiation, low production of toxic ROS.

Described herein is a method for making a croconaine compound which comprises reacting a halothiophene with an alkanolamine and a catalyst under heating conditions, isolating and purifying the resulting aminothiophene, modifying the aminothiophene, reacting croconic acid and the modified aminothiophene in a solvent under reflux conditions to form the croconaine compound, and isolating and purifying the compound.

These and other features, aspects and advantages of the present disclosure will become better understood with reference to the following description and appended claims.

BRIEF DESCRIPTION OF THE DRAWINGS

FIG. 7 depicts several examples of substituents where Q represents alkyl as defined herein, Y represents aryl as defined herein, and X represents halogen as defined herein.

DETAILED DESCRIPTION

Figure 1:
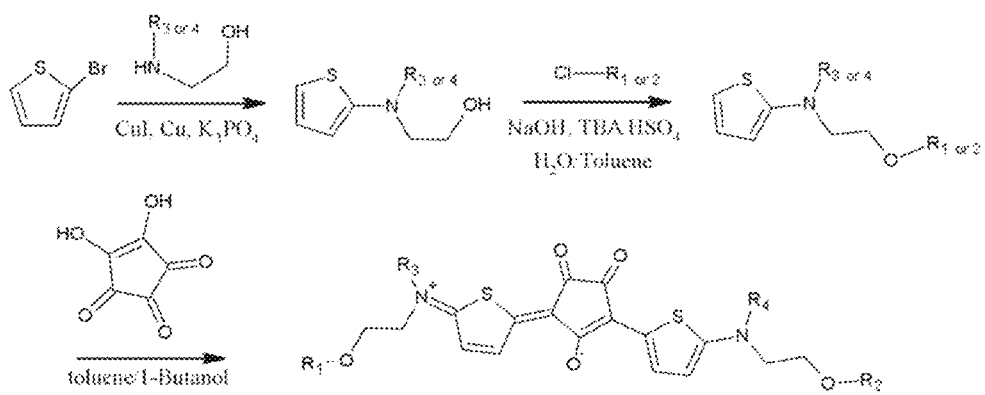
FIG. 1 depicts a scheme of synthesis of a compound of formula (I).

The croconaine compounds are one or more compounds of formula (I):

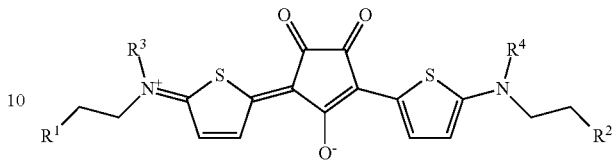

(I)

wherein R$^1$ and R$^2$ are each independently selected from the group consisting of —H, alkyl, substituted alkyl, arylalkyl, aryl, substituted aryl, heteroaryl, substituted heteroaryl, carboxylic acid, alkoxy, aryloxy, polyethylene glycol, amino, dialkylamino, halogen, triazole, amido, N-alkylamido, sulfone, sulfonate, phosphonate, and a first reactive group, R$^3$ and R$^4$ are each independently selected from the group consisting of —H, alkyl, substituted alkyl, arylalkyl, aryl, substituted aryl, heteroaryl, substituted heteroaryl, carboxylic acid, and a second reactive group, or wherein R$^1$ and R$^3$ taken together form an optionally substituted 5- or 6-membered ring, or wherein R$^2$ and R$^4$ taken together form an optionally substituted 5- or 6-membered ring, or a pharmaceutically acceptable salt, optical isomer, geometric isomer or tautomers thereof.

Reactive groups for conjugation include, but are not limited to, alkyl hydroxysuccinimide ester, alkyl maleimide, alkyl isothiocyanate, alkyl azide, alkyl alkyne, alkyl haloacetamido, aryl ester, aryl hydroxysuccinimide ester, aryl maleimide, aryl isothiocyanate, aryl azide, aryl alkyne, aryl haloacetamido, alkoxy hydroxysuccinimide ester, alkoxy maleimide, alkoxy isothiocyanate, alkoxy azide, alkoxy alkyne, alkoxy haloacetamido, aryloxy ester, aryloxy hydroxysuccinimide ester, aryloxy maleimide, aryloxy isothiocyanate, aryloxy azide, aryloxy alkyne, and aryloxy haloacetamido. FIG. 7 illustrates several such substituents, where Q is an alkyl, Y is aryl, X is halo, and the wavy line indicates the point of attachment to R$^1$, R$^2$, R$^3$ or R$^4$.

Specific examples of compounds of formula (I) include the following compounds 1-4:

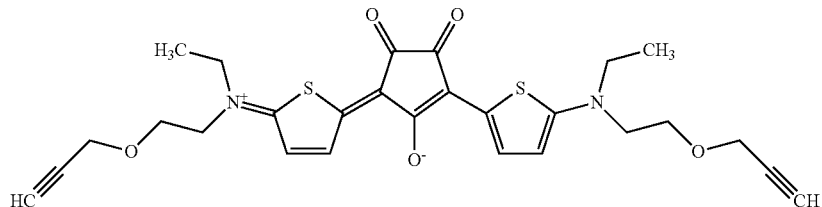

(1)

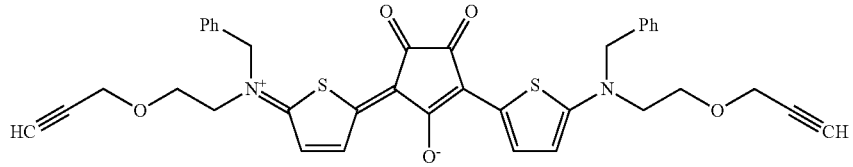

(2)

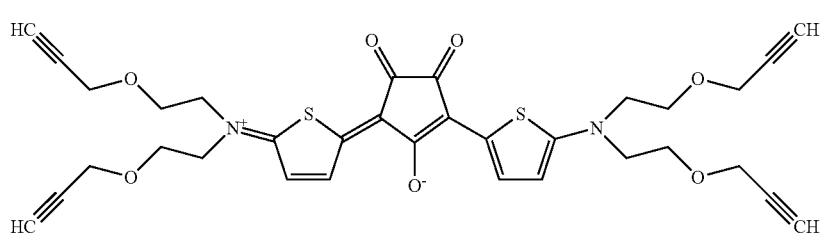

(3)

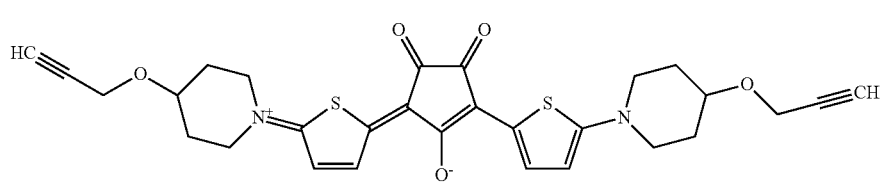

(4)

As used in the present disclosure, the following words, phrases, and symbols are generally intended to have the meanings set forth below. The following abbreviations and terms have the indicated meanings throughout.

A dash ("-") that is not between two letters or symbols is used to indicate a point of attachment for a substituent. For example, —CONH$_2$ is attached through the carbon atom to another atom of a molecule, such as an atom of formula (I) substituted by an R group wherein the R group can be —CONH$_2$.

As used herein the term "alkenyl" refers to a straight or branched chain aliphatic hydrocarbon having two to twelve carbon atoms, preferably two to six, and containing one or more carbon-to-carbon double bonds, which may be optionally substituted as herein further described, with multiple degrees of substitution being allowed. Examples of "alkenyl" as used herein include, but are not limited to, ethenyl, propenyl, butenyl, and the like.

The term "alkoxy" as used herein alone or in combination refers to an alkyl, alkenyl or alkynyl group bound through a single terminal ether linkage. Examples of alkoxy groups include, but are not limited to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, 3-methylpentoxy, fluoromethoxy, difluoromethoxy, trifluoromethoxy, chloromethoxy, dichloromethoxy, and trichloromethoxy.

"Alkyl" by itself or as part of another substituent refers to a saturated or unsaturated, branched, or straight-chain monoradical hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 20 carbon atoms, in certain embodiments, from 1 to 10 carbon atoms, in certain embodiments, from 1 to 8 or 1 to 6 carbon atoms, and in certain embodiments from 1 to 3 carbon atoms.

As used herein, "alkyl linker" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—CH$_2$—), ethyl (—CH$_2$CH$_2$—), n-propyl (—CH$_2$CH$_2$CH$_2$—), i-propyl (—CHCH$_3$CH$_2$—), n-butyl (—CH$_2$CH$_2$CH$_2$CH$_2$—), s-butyl (—CHCH$_3$CH$_2$CH$_2$—), i-butyl (—C(CH$_3$)$_2$CH$_2$—), n-pentyl (—CH$_2$CH$_2$CH$_2$CH$_2$CH$_2$—), s-pentyl (—CHCH$_3$CH$_2$CH$_2$CH$_2$—) or n-hexyl (—CH$_2$CH$_2$CH$_2$CH$_2$CH$_2$CH$_2$—).

As used herein the term "alkynyl" refers to a straight or branched chain aliphatic hydrocarbon having two to twelve carbon atoms, preferably two to six, and containing one or more carbon-to-carbon triple bonds, which may be optionally substituted as herein further described, with multiple degrees of substitution being allowed. Examples of "alkynyl" as used herein include, but are not limited to, vinyl, allyl, and propargyl.

"Amido" refers to a group —C(O)NR$^5$R$^6$, wherein R$^5$ and R$^6$ are independently selected from —H, $C_{1-4}$ alkyl, phenyl and $C_{7-10}$ arylalkyl as defined herein.

"Amino" refers to a group —NR$^5$R$^6$, wherein R$^5$ and R$^6$ are independently selected from —H, $C_{1-4}$ alkyl, phenyl, and $C_{7-10}$ arylalkyl as defined herein.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene, bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

The term "arylalkyl" refers to an aryl group, as defined herein, attached through an alkyl linker. As one example, the term includes benzyl.

The term "aryloxy" as used herein alone or in combination refers to an aryl group bound through a single terminal ether linkage. Non-limiting exemplary aryloxy groups include benzyloxy and phenethoxy.

"Carboxylic ester" refers to —C(O)OR$^7$, wherein R$^7$ is an alkyl group, an aryl group or a heteroaryl group as defined herein.

"Halogen" is typically a fluorine, chlorine, bromine or iodine atom.

"Halo" refers to —F, —Cl, —Br, or —I as a substituent.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, γ-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments heteroaryl groups are those derived from thiophene, pyrrole, benzothiophene, benzofuran, indole, pyridine, quinoline, imidazole, oxazole, and pyrazine.

As used herein, the term "maleimide" refers to the chemical compound with the formula $H_2C_2(CO)_2N—$.

"Phosphonate" refers to a group —PO(OH)$_2$, or —PO(OR$^{13}$)$_2$ wherein R$^{13}$ is alkyl or aryl as defined above.

As used herein, the term "polyethylene glycol" refers to a polymer containing ethylene glycol monomer units of formula —O—CH$_2$—CH$_2$—. Suitable polyethylene glycols may have a free hydroxyl group at each end of the polymer molecule, or may have one or more hydroxyl groups etherified with an alkyl, e.g., a methyl group. Also suitable are derivatives of polyethylene glycols having esterifiable carboxy groups. Polyethylene glycols useful in the present disclosure can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to, polyethylene glycol-200, polyethylene glycol-300, polyethylene glycol-400, polyethylene glycol-600, and polyethylene glycol-900. The number following the dash in the name refers to the average molecular weight of the polymer.

As used herein, the term "hydroxysuccinimide ester" refers to a cyclic imide with the formula $C_5H_4NO_4—$.

"Sulfonate" refers to a group —SO$_3$H.

"Sulfone" refers to a group —SO$_2$R$^8$, wherein R$^8$ is independently selected from —H, $C_{1-4}$ alkyl, phenyl and $C_{7-10}$ arylalkyl.

As used herein, the term "triazole" refers to the structures: 1,2,3-triazole:

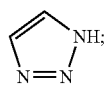

(5)

and 1,2,4-triazole:

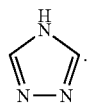

(6)

"Substituted" refers to a group in which one or more hydrogen atoms are independently replaced with the same or different substituent(s). Examples of substituents include, but are not limited to, —X, —R$^9$, —CH$_2$CH$_2$R$^9$, —O—, (—OH), =O, —OR$^9$, —SR$^9$, —S—, =S, —NR$^9$R$^{10}$, =NR$^9$, —CX3, —CN, —CF3, —OCN, —SCN, —NO, —NO$_2$, =N$_2$, —N$_3$, —S(O)$_2$O—, —S(O)$_2$OH, —S(O)$_2$R$^9$, —OS(O$_2$)O—, —OS(O)$_2$R$^9$, —P(O)(O—)$_2$, —P(O)(OR$^9$) (O—), —OP(O)(OR$^9$)(OR$^{10}$), —C(O)R$^9$, —C(S)R$^9$, —C(O)OR$^9$, —C(O)NR$^9$R$^{10}$, —C(O)O—, —C(S)OR$^9$, —NR$^{11}$C(O)NR$^9$R$^{10}$, —NR$^{11}$(S)NR$^9$R$^{10}$, —NR$^{11}$C(NR$^{12}$) NR$^9$R$^{10}$, —C(NR$^{11}$)NR$^9$R$^{10}$, —S(O)$_2$, NR$^9$R$^{10}$, —NR$^{12}$S (O)$_2$R$^9$, —NR$^{12}$C(O)R$^9$, and —S(O)R$^9$ where each —X is independently a halogen; each R$^9$ and R$^{10}$ are independently hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or R$^9$ and R$^{10}$ together with the nitrogen atom to which they are bonded to form a heterocyclyl, substituted heterocyclyl, heteroaryl, or substituted heteroaryl ring, and R$^{11}$ and R$^{12}$ are independently hydrogen, alkyl, substituted alkyl, aryl, substituted aryl, arylalkyl, substituted arylalkyl, cycloalkyl, substituted cycloalkyl, heterocyclyl, substituted heterocyclyl, heteroaryl, substituted heteroaryl, or heteroarylalkyl, or R$^{11}$ and R$^{12}$ together with the atom to which they are bonded form one or more heterocyclyl, substituted heterocyclyl, heteroaryl, or substituted heteroaryl rings. In certain embodiments, a tertiary amine or aromatic nitrogen may be substituted with an oxygen atom to form the corresponding nitrogen oxide.

Selected substituents within the compounds described herein may be present to a recursive degree. In this context, "recursive substituent" means that a substituent may recite another instance of itself. Because of the recursive nature of such substituents, theoretically, a large number of substituents may be present in any given claim. One of ordinary skill in the art of medicinal chemistry and organic chemistry understands that the total number of such substituents is reasonably limited to the desired properties of the compound intended. Such properties include, by way of non-limiting example, physical properties such as molecular weight, solubility or log P, application properties such as activity against the indented target, and practical properties such as ease of synthesis. In certain embodiments, a recursive substituent comprises from 1 to 20 carbon and/or heteroatoms; in certain embodiments, from 1 to 10 carbon and/or hetero atoms; in certain embodiments, from 1 to 8 or 1 to 6 carbon and/or heteroatoms; and in certain embodiments from 1 to 3 carbon and/or heteroatoms.

Recursive substituents are an intended aspect of this disclosure. One of ordinary skill in the art of medicinal and organic chemistry understands the versatility of such substituents. To the degree that recursive substituents are present in an embodiment, the total number will be determined as set forth above.

When any variable occurs more than one time in any constituent or in any formula, its definition on each occurrence is independent of its definition at every other occurrence. Thus, for example, if a group is shown to be substituted with 0-3 R$^4$ substituents, then said group may optionally be substituted with up to three R$^4$ substituents, and R$^4$ at each occurrence is selected independently from the defined list of possible R$^4$ substituents. Also, by way of example, for the group —N(R$^5$)$_2$, each of the two R$^5$ substituents on N is independently selected from the defined list of possible R$^5$ substituents. Combinations of substituents and/or variables are permissible when such combinations result in stable compounds. By "stable compound" or "stable structure" is meant herein a compound that is sufficiently robust to survive isolation to a useful degree of purity from a reaction mixture, and to survive formulation into an efficacious agent, for example, a diagnostic or therapeutic agent.

The term "extraction" refers to the mass transfer operation whereby solute from a first solvent moves to a second, immiscible solvent.

The term "in vacuo" as used herein refers to under the pressure that is lower than atmospheric pressure.

"Inert gas" as used herein refers to a gas which does not undergo chemical reactions with starting materials, reagents, intermediates or products under the reaction conditions described herein. Inert gases include, but are not limited to, nitrogen (N), neon (Ne), argon (Ar), and krypton (Kr).

The term "light source" as used herein refers to a laser, light emitting diode (LED), or lamp.

"Reflux conditions" as used herein refers to conditions wherein a liquid boils, and the vapor of the boiling liquid condenses and runs back down into the liquid below.

The term "room temperature" refers to the temperature range of about 20° C. to about 25° C.

"Silica gel chromatography" as used herein is understood to include chromatography on a column packed with silica gel, elution, collection of fractions, and combination of those fractions shown by thin layer chromatography (TLC) to contain the desired product free of starting material and impurities. The following additional abbreviations are used in this disclosure:
CAS Chemical Abstract Service
CHCl$_2$ Chloroform
Cu Copper
CuBr Copper(I) Bromide
CuI Copper(I) Iodide
DCM Dichloromethane
DIPEA Diisopropylethylamine
DMF Dimethylformamide
DMSO Dimethyl sulfoxide
Et$_3$N Triethyl amine
H$_2$SO$_4$ Sulfuric Acid
K$_2$PO$_4$ Potassium Phosphate, Dibasic
MeCN Acetonitrile
MeOH Methanol
PBS Phosphate Buffered Saline
TBA Tetrabutylammonium
TBTA Tris-(benzyltriazolylmethyl)amine
THF Tetrahydrofuran Starting materials, solvents, and reagents can be procured from material suppliers such as Sigma-Aldrich, Alfa Aesar, VWR, Fisher, Fluka, Acro Organics, and/or other suppliers, as may be required and/or desired in a particular embodiment.

Use for Thermal Imaging.

Molecules or nanoparticles that contain one or more croconaine compounds can be delivered to sites of pathological disease such a tumor or bacterial infection by local delivery methods such as injection or topical ointment, or systemic delivery methods such as intravenous injection, or oral administration. A diffuse light source with low power and a wavelength band that covers the range of about 650 nm to about 900 nm can be used to illuminate the site of disease. In some embodiments, a wavelength of about 700 nm to about 900 nm can be used to illuminate the site of disease. In some embodiments, a wavelength of about 750 nm to about 900 nm can be used to illuminate the site of disease. In some embodiments, a wavelength of about 750 nm to about 850 nm can be used to illuminate the site of disease. In some embodiments, a wavelength of to about 780 nm to about 820 nm can be used to illuminate the site of disease. In some embodiments, a wavelength of about or exactly 780, 785, 790, 795, 800, 805, 810, 815, or 820 nm can be used to illuminate the site of disease. The small amount of heat that is generated can be detected by sensitive thermal imaging methods such as acoustic imaging which identifies the site of disease with high resolution.

Use for Destroying Aberrant Tissue.

Molecules or nanoparticles that contain one or more croconaine compounds can be delivered to sites of pathological disease such a tumor or bacterial infection. A light source with moderate power and a wavelength band in the range of about 650 nm to about 900 nm can be used to irradiate the site of disease. In some embodiments, a wavelength of about 700 nm to about 900 nm can be used to irradiate the site of disease. In some embodiments, a wavelength of about 750 nm to about 900 nm can be used to irradiate the site of disease. In some embodiments, a wavelength of about 750 nm to about 850 nm can be used to irradiate the site of disease. In some embodiments, a wavelength of to about 780 nm to about 820 nm can be used to irradiate the site of disease. In some embodiments, a wavelength of about or exactly 780, 785, 790, 795, 800, 805, 810, 815, or 820 nm can be used to irradiate the site of disease. The strong heat that is generated produces localized death of the pathological cells.

Use for Wound Sealing.

A wound is treated with protein material that also contains croconaine compound and a light source with a wavelength band in the range of about 650 nm to about 900 nm is used irradiate the wound. In some embodiments, a wavelength of about 700 nm to about 900 nm can be used to irradiate the wound. In some embodiments, a wavelength of about 750 nm to about 900 nm can be used to irradiate the wound. In some embodiments, a wavelength of about 750 nm to about 850 nm can be used to irradiate the wound. In some embodiments, a wavelength of about 780 nm to about 820 nm can be used to irradiate the wound. In some embodiments, a wavelength of about or exactly 780, 785, 790, 795, 800, 805, 810, 815, or 820 nm can be used to irradiate the wound. The photothermal heating denatures the protein material and leads to sealing of the wound.

Use for Light Activated Drug Release.

Polymers or nanocapsules containing pharmaceutical agents are delivered to sites of disease in a living subject, and a light source with a wavelength band in the range of about 650 nm to about 900 nm is used irradiate the site of disease. In some embodiments, a wavelength of about 700 nm to about 900 nm can be used to irradiate the site of disease. In some embodiments, a wavelength of about 750 nm to about 900 nm can be used to irradiate the site of disease. In some embodiments, a wavelength of about 750 nm to about 850 nm can be used to irradiate the site of disease. In some embodiments, a wavelength of to about 780 nm to about 820 nm can be used to irradiate the site of disease. In some embodiments, a wavelength of about or exactly 780, 785, 790, 795, 800, 805, 810, 815, or 820 nm can be used to irradiate the site of disease. The heat that is generated disrupts the polymer or nanocapsule structure and releases of the pharmaceutical agent.

The following Examples are intended to illustrate the present disclosure and should not be construed as to narrow its scope. One skilled in the art will readily recognize that the Examples suggest many other ways in which additional embodiments could be practiced. It should be understood that numerous variations and modifications may be made while remaining within the scope of the disclosure.

EXAMPLES

The merits of the method for making the croconaine compound of this disclosure will become apparent with reference to the following examples. The method of this application should not be restricted to the following examples.

Example 1

Synthesis of Compound I

This example describes a general synthesis of compounds of formula I. With reference to FIG. 1:

Synthesis of the Aminothiophene.

A halothiophene is contacted with an alkanolamine, copper, copper (I) iodide, and potassium phosphate tribasic, in a suitable solvent or solvent mixture, and heated. Such suitable solvents include polar protic solvents such as 2-(ethylamino) ethanol, dimethylethanolamine, and/or other solvents, as may be required and/or desired in a particular embodiment. In some embodiments, the mixture is heated to 70-90° C. In some embodiments, the mixture is heated to 70, 75, 80, 85, or 90° C. In some embodiments, the mixture is heated for 15-25 hours. In some embodiments, the mixture is heated for 15, 16, 17, 18, 19, 20, 21, 22, 23, 24, or 25 hours. The resulting mixture is typically cooled prior to workup and/or isolation. The crude product can be isolated. Such isolation can be achieved by techniques such as liquid extraction, precipitation, recrystallization, Soxhlet extraction, and/or other techniques, as may be required and/or desired in a particular embodiment. The crude product can be purified. Such purification can be achieved by techniques such as HPLC, precipitation, recrystallization, silica gel chromatography, size-exclusion chromatography, solvent washing, and/or other techniques, as may be required and/or desired in a particular embodiment.

Modification of Aminothiophene.

A desired structural group is appended to the hydroxyl group of the aminothiophene by contacting the aminothiophene with a structural group containing a chloro-group in a suitable solvent or solvent mixture and stirred. Such suitable solvents and/or solvent mixtures include toluene/NaOH$_{(aq)}$, chloroform/NaO$_{(aq)}$, a nonpolar organic solvent immiscible with water/aqueous base, polar organic solvent (such as DMF, DMSO, or MeCN)/aqueous base (such as DIPEA, or $K_2CO_3$), and/or other solvents, as may be required and/or desired in a particular embodiment. In some embodiments, the mixture is stirred for 24-48 hours. In some embodiments, the mixture is stirred for 24, 30, 36, 42, or 48 hours. The crude product can be isolated. Such isolation can be achieved by techniques such as liquid extraction, precipitation, recrystallization, Soxhlet extraction, and/or other techniques, as may be required and/or desired in a particular embodiment. The crude product can be purified. Such purification can be achieved by techniques such as HPLC, precipitation, recrystallization, silica gel chromatography, size-exclusion chromatography, solvent washing, and/or other techniques, as may be required and/or desired in a particular embodiment.

Formation of Croconaine Compound.

The aminothiophene is contacted with croconic acid in a suitable solvent and/or solvent mixture, and heated. Such suitable solvents and/or solvent mixtures include ethanol, toluene/butanol, benzene/butanol, benzene/isopropanol, toluene/isopropanol, and/or other solvents, as may be required and/or desired in a particular embodiment. In some embodiments, the mixture is heated to 120-130° C. In some embodiments, the mixture is heated to 120, 121, 122, 123, 124, 125, 126, 127, 128, 129, or 130° C. In some embodiments, the mixture is heated for 45-75 minutes. In some embodiments, the mixture is heated for 45, 50, 55, 60, 65, 70, or 75 minutes. The resulting mixture is cooled. The crude product can be isolated. Such isolation can be achieved by techniques such as liquid extraction, precipitation, recrystallization, Soxhlet extraction, and/or other techniques, as may be required and/or desired in a particular embodiment. The crude product can be purified. Such purification can be achieved by techniques such as HPLC, precipitation, recrystallization, silica gel chromatography, size-exclusion chromatography, solvent washing, and/or other techniques, as may be required and/or desired in a particular embodiment.

Example 2

Synthesis of Compound 1

Figure 2:
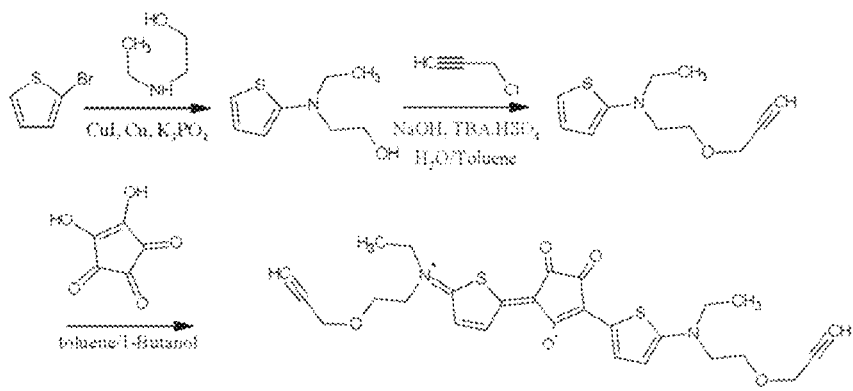
FIG. 2 depicts a scheme of synthesis of compound (1).

This example describes the synthesis of compound 1. With reference to FIG. 2:

Commercially available solvents and chemicals were used without further purification unless otherwise stated. Water was de-ionized and microfiltered. Cu(I)TBTA.Br was synthesized from CuBr and TBTA, and stored in a desiccator prior to use. Aminothiophenes are known to be relatively unstable. Consequently, any purification by column chromatography was undertaken after pre-treating the column with 3% $Et_3N$/hexane solution, and the isolated pure compounds were stored at −20° C.

Synthesis of the Aminothiophene.

2-Bromothiophene (1.19 mL, 12.3 mmol, CAS 1003-09-4), copper(I) iodide (350 mg, 15 mol %), copper powder (117 mg, 15 mol %, CAS 7440-50-8) and potassium phosphate tribasic (5.22 g, 24.6 mmol) were suspended in 2-(ethylamino)ethanol (12 mL) and heated at 80° C. for 20 h under Ar. After this time, the reaction mixture was allowed to cool to room temperature and water (40 mL) added. The solution was extracted with diethyl ether (3×40 mL), and the combined organic fractions washed with brine (1×60 mL), dried over $MgSO_4$ and the solvent removed in vacuo. Purification was undertaken by silica gel column chromatography (column loaded using 3% $Et_3N$/hexane) using 2:1 hexane/ethyl acetate to elute the product as an orange oil (1.02 g, 5.96 mmol, 48%).

Modification of Aminothiophene.

To a solution of 2-(ethyl(thiophen-2-yl)amino)ethanol (1.01 g, 5.90 mmol) and propargyl chloride (1.54 mL, 21.2 mmol) in toluene (35 mL) was added a solution of tetrabutylammonium bisulfate (200 mg) in 50% sodium hydroxide solution (20 mL) and the reaction mixture was stirred at room temperature for 3 days. The organic layer was separated and the solvent removed in vacuo. The resulting residue was dissolved in $CHCl_3$ (100 mL), washed with water (2×50 mL), dried over $MgSO_4$ and the solvent removed in vacuo. Purification was undertaken by silica gel column chromatography (column loaded using 3% $Et_3N$/hexane) using 5% ethyl acetate/hexane to elute the product as an off-white solid (810 mg, 3.87 mmol, 67%).

Formation of Croconaine Compound.

Croconic acid (136 mg, 0.96 mmol, CAS 488-86-8) and N-ethyl-N-(2-(prop-2-yn-1-yloxy)ethyl)thiophen-2-amine (400 mg, 1.91 mmol) were dissolved in 1:1 anhydrous toluene/1-butanol (30 mL) and heated at reflux for 1 h under Ar. After this time, the solution was allowed to cool to room temperature and the solvent removed in vacuo. The crude residue was purified by silica gel column chromatography using 2% MeOH/DCM to elute the product as a black solid (373 mg, 0.71 mmol, 74%).

Example 3

Heating with Compound 1

This example describes a method of using compound 1 to increase the temperature of a solution. A 0.6 mL solution of compound 1 in 4:1 $MeOH/H_2O$ at 2.0 or 50.0 µg/mL was stirred using a magnetic stirrer bar in a 1 cm Helma cuvette located in an air-conditioned room maintained at 295 K. An Omega hypodermic thermocouple (HYPO-33-1-T-G-60-SMPW-M) was placed in the solution and the temperature measured using the associated USB converter. The Ti:Sapphire laser beam was aligned to pass through the solution (above the stirrer and avoiding close contact with the thermocouple) in an identical manner in every experiment. The laser wavelength was set at 780 and the power controlled to be 250 mW during all of the experiments, with a beam diameter of 0.3 cm. Hence, the laser power density was 3.5 $W/cm^2$.

The resulting temperature changes were recorded as seen in Table 1 below.

TABLE 1

Temperature changes observed for different solutions of compound 1 (4:1 Me/OH/$H_2O$) during laser irradiation (780 nm, 250 mW) and the corresponding absorbance values (A).

| Concentration/ µg/mL | ΔT/° C. | A |
|---|---|---|
| 50.0 | 11.3 | 22.4 (est) |
| 5.00 | 11.0 | 2.24 |
| 2.50 | 10.4 | 1.13 |
| 1.67 | 9.8 | 0.73 |
| 1.00 | 7.2 | 0.46 |
| 0.50 | 3.4 | 0.22 |
| 0.25 | 2.0 | 0.11 |
| 0.10 | 0.1 | 0.04 |

Example 4

Photothermal Properties of Croconaine 1

Figure 8:
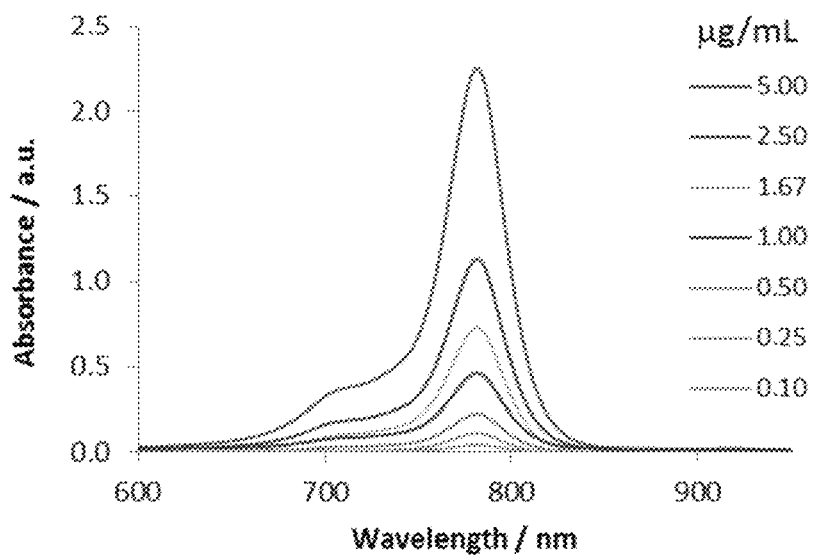
FIG. 8 shows the absorbance spectra of croconaine 1 (4:1 MeOH/H$_2$O) at different concentrations.
Figure 9:
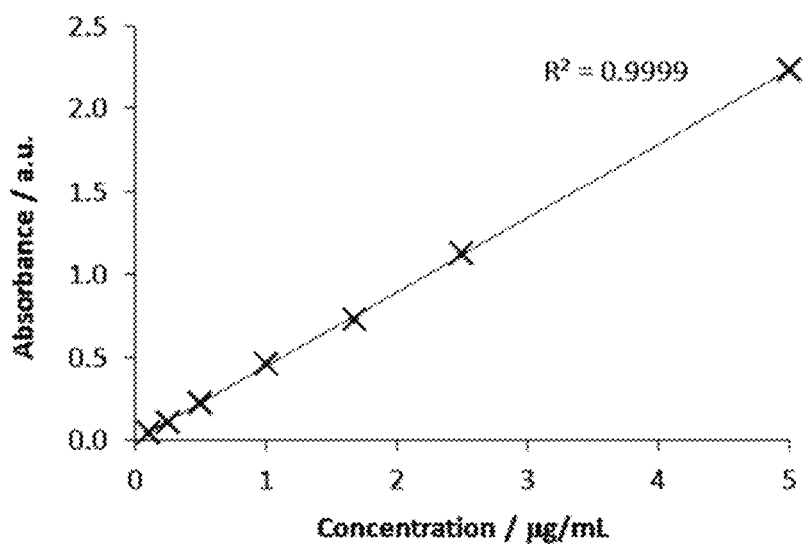
FIG. 9 shows a graph of croconaine 1 concentration against absorbance at 780 nm (4:1 MeOH/H$_2$O), proving a linear relationship obeying the Beer-Lambert Law (A=ϵ.c.l).

The data in FIGS. 8 and 9 show that the absorbance of croconaine 1 obeys the Beer-Lambert Law (A=ϵ.c.l).

Figure 10:
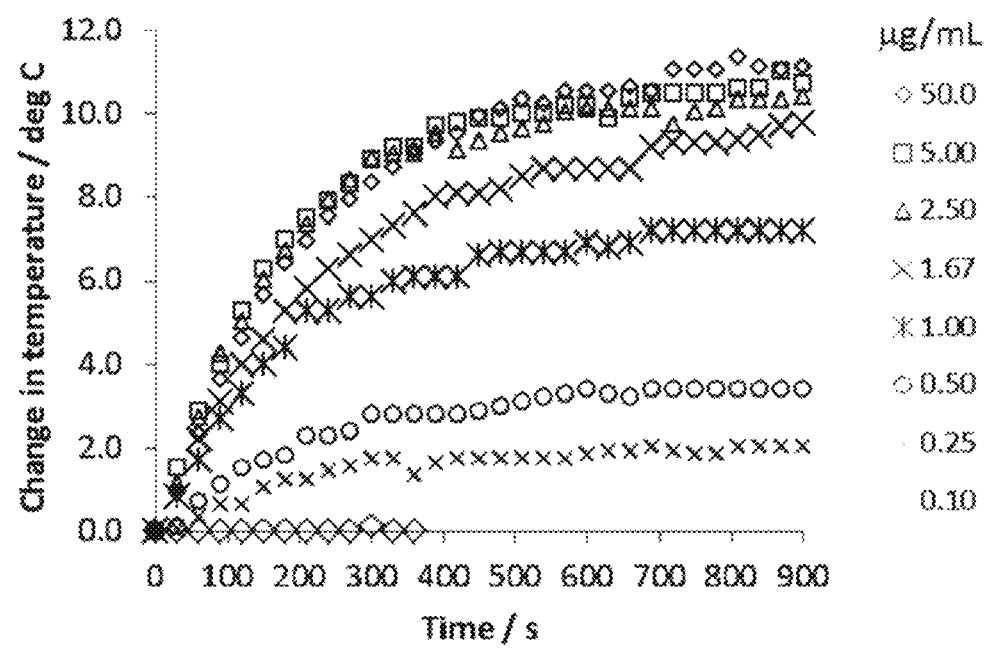
FIG. 10 shows temperature changes observed for different concentrations of croconaine 1 (4:1 MeOH/H$_2$O) during laser irradiation at 780 nm. Laser power controlled to be 250 mW.
Figure 11:
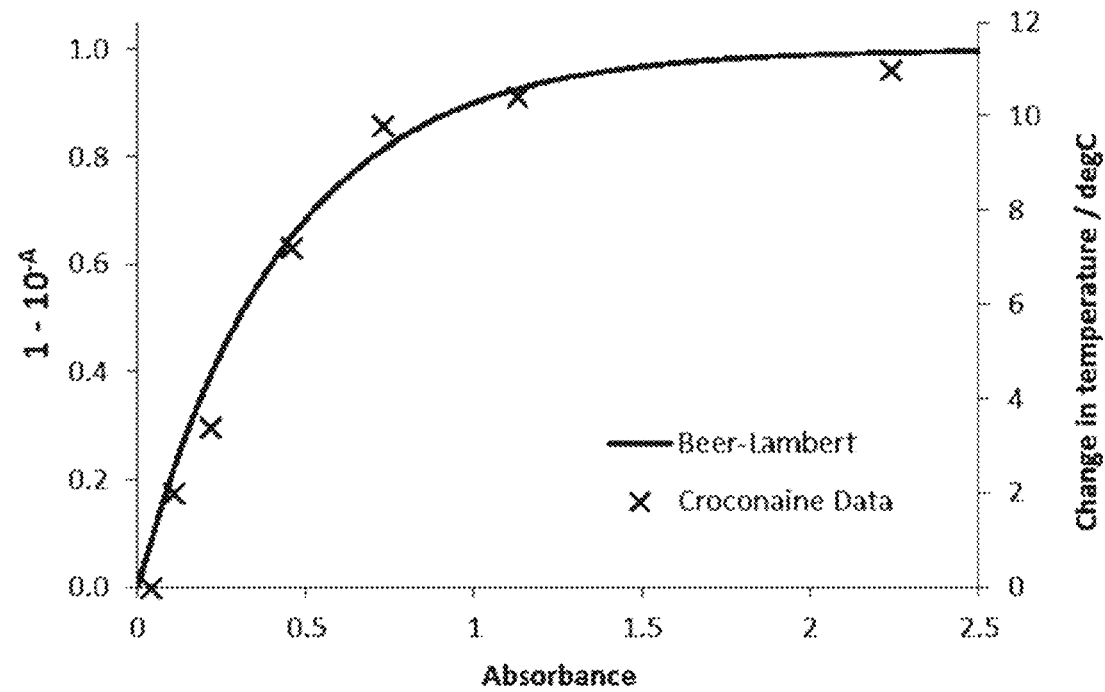
FIG. 11 shows plots of the Beer-Lambert Law and maximum temperature change against absorbance of different laser wavelengths by croconaine compound 1. Laser power controlled to be 250 mW.

The data in Table 1, FIGS. 10 and 11 show that the heating produced by croconaine 1 due to absorption of 780 nm laser light also obeys the Beer-Lambert Law. Heating is linear with absorbance from about A=0 until about A=1, and when A>1, the additional heating provided by increasing the absorbance decreases.

Figure 12:
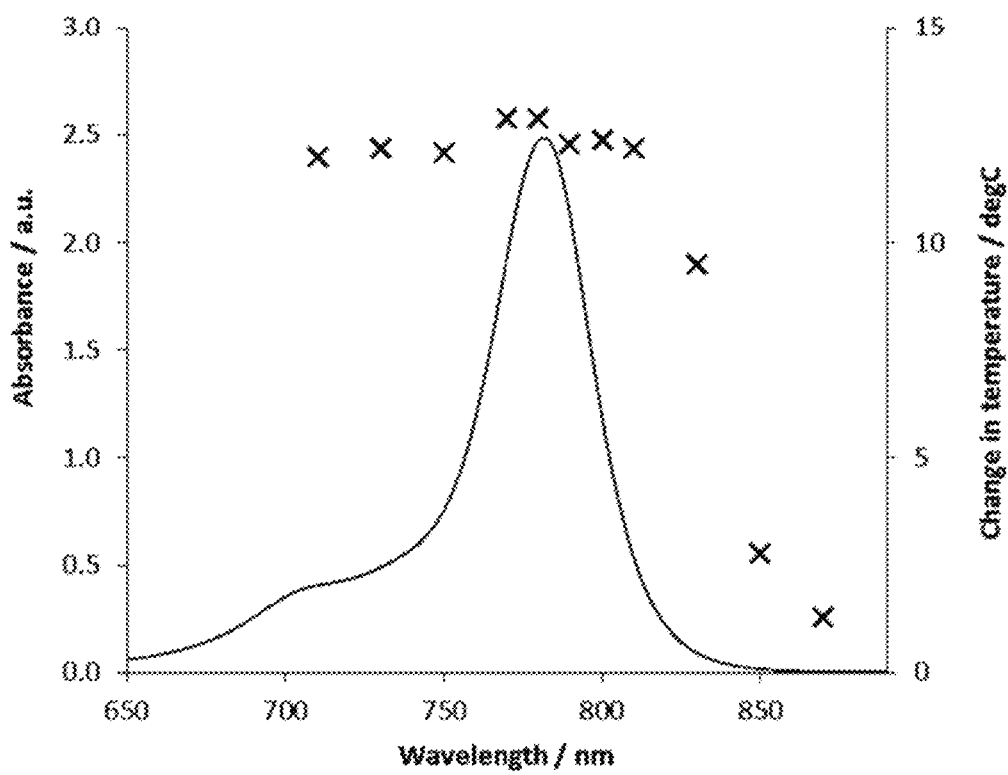
FIG. 12 shows absorbance spectrum for croconaine 1 (red line) and temperature changes upon laser irradiation (blue crosses) at different wavelengths (4:1 MeOH/H$_2$O, 0.005 mg/mL for absorbance, 0.05 mg/mL for laser experiments).

The data in FIG. 12 shows that laser irradiation of croconaine 1 at different wavelengths produces heating that is proportional to the amount of light absorbed by the compound. These experiments were conducted in 4:1 $MeOH/H_2O$, with 0.005 mg/mL of compound for absorbance, 0.05 mg/mL of compound for laser experiments.

Figure 13:
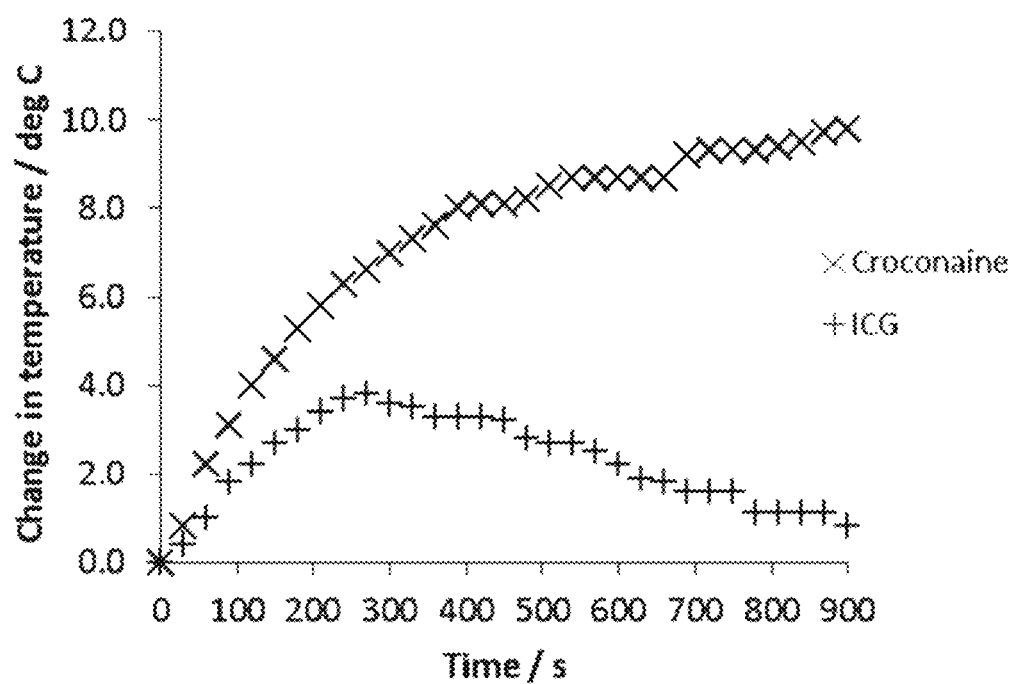
FIG. 13 shows temperature changes observed for solutions of croconaine 1 and ICG (4:1 MeOH/H$_2$O, 1.67 and 2.00 µg/mL respectively) during laser irradiation at 780 nm. Laser power controlled to be 250 mW.
Figure 14:
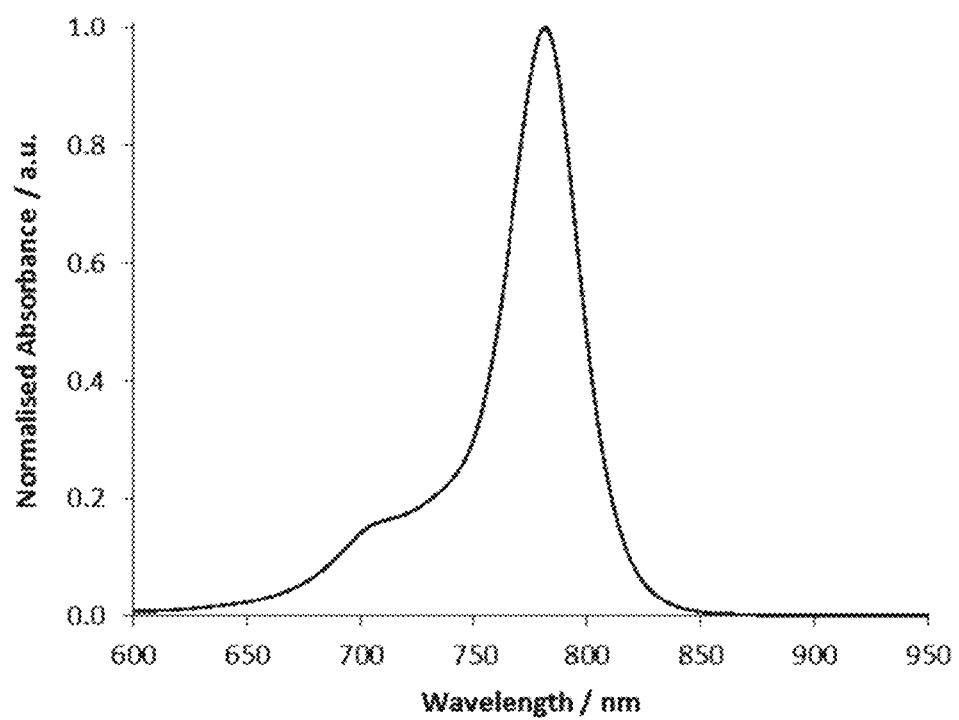
FIG. 14 shows that there is no change in the normalised absorbance spectrum of croconaine 1 (4:1 MeOH/H$_2$O, 0.005 mg/mL) after laser irradiation at 810 nm (900 s, 260 mW).
Figure 15:
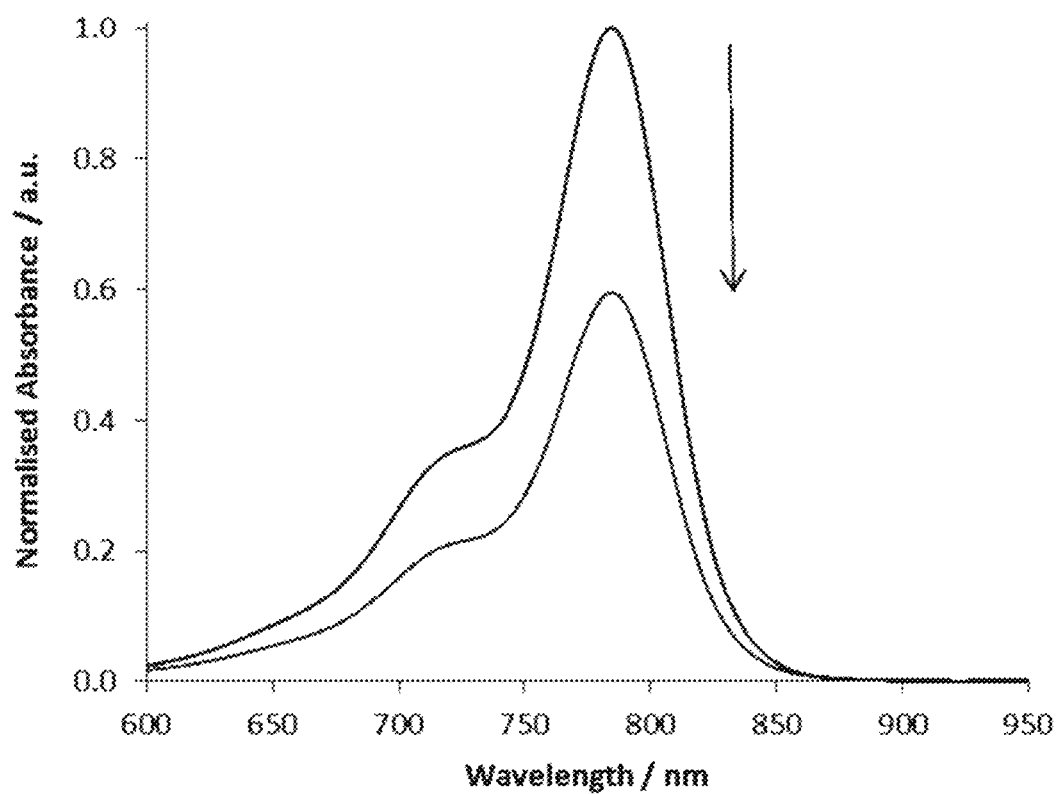
FIG. 15 shows a drop in the normalised absorbance of ICG (4:1 MeOH/H$_2$O, 0.005 mg/mL) after laser irradiation at 810 nm (900 s, 260 mW).

The data in FIG. 13 shows that extended near-infrared irradiation of indocyanine green (ICG) leads to loss of heating effect due to photobleaching of the compound (a major performance problem), but there is no heating effect loss with the croconaine 1, indicating that it is photostable over the entire 15 minute heating period. These experiments were conducted in 4:1 $MeOH/H_2O$, with 1.67 µg/mL of croconaine 1 and 2.00 µg/mL of ICG respectively. This difference in compound photobleaching was confirmed with studies that looked at changes in the compound absorption signal. As shown in FIG. 14, 810 nm laser irradiation produced no change in the absorbance for croconaine 1, but FIG. 15 shows almost 50% decrease in the absorbance for ICG (major photobleaching).

Figure 16:
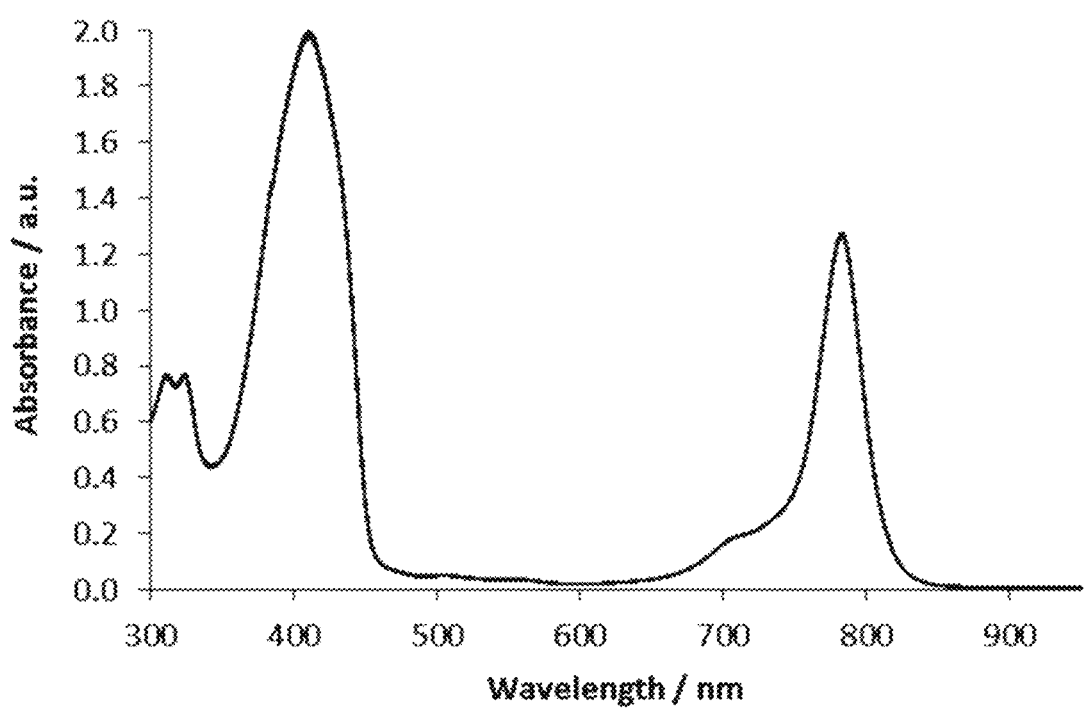
FIG. 16 shows the change in the absorption spectra of a solution of croconaine 1 (5.0 µM) and DPBF (100 µM) upon Xenon lamp irradiation (>620 nm) after 0, 1, 2 and 3 minutes (99:1 MeOH/CHCl$_3$).
Figure 17:
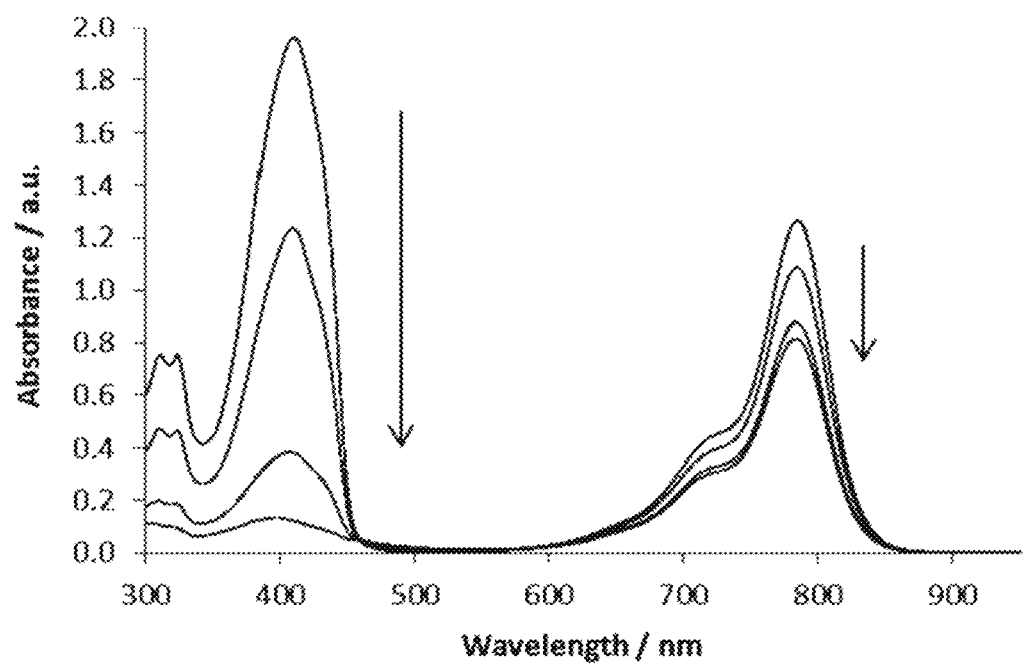
FIG. 17 shows the change in the absorption spectra of a solution of ICG (5.0 µM) and DPBF (100 µM) upon Xenon lamp irradiation (>620 nm) after 0, 1, 2 and 3 minutes (99:1 MeOH/CHCl$_3$).

Another photothermal performance property exhibited by croconaine 1 is its inability to photogenerate singlet oxygen, a reactive chemical that can cause material fatigue and biological effects. Shown in FIGS. 16 and 17 are singlet oxygen trapping experiments that use the chemical trap DPBF to react with any singlet oxygen that is produced. Thus, the presence of singlet oxygen is detected by a decrease in the DPBF absorbance band at 400 nm. Experiments monitored the change in the absorption spectra of a solution of croconaine 1 (5.0 μM) and DPBF (100 μM) in 99:1 MeOH/CHCl$_3$ with Xenon lamp irradiation (>620 nm) after 0, 1, 2 and 3 minutes. As seen in FIG. 16 there is a no change in the 400 nm band thus indicating no singlet oxygen is produced by irradiating croconaine 1. This outcome is in contrast to the results in FIG. 17 which show that irradiating ICG under the same experimental conditions (ICG (5.0 μM) and DPBF (100 μM) in 99:1 MeOH/CHCl$_3$ with Xenon lamp irradiation (>620 nm) for 0, 1, 2 and 3 minutes) leads to rapid loss of the DPBF absorbance band at 400 nm due to its reaction with the singlet oxygen that is produced.

Example 5

Synthesis of Compound 2

Figure 3:
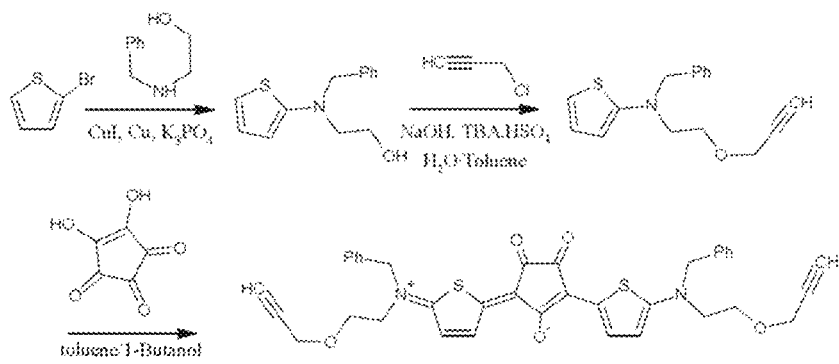
FIG. 3 depicts a scheme of synthesis of compound (2).

This example describes the synthesis of compound 2. With reference to FIG. 3:

Commercially available solvents and chemicals were used without further purification unless otherwise stated. Such materials can be procured from material supplies such as Sigma-Aldrich, Alfa Aesar, VWR, Fisher, Fluka, Acro Organics, and/or other suppliers, as may be required and/or desired in a particular embodiment. Water was de-ionized and microfiltered. Cu(I)TBTA.Br was synthesized from CuBr and TBTA, and stored in a desiccator prior to use. Aminothiophenes are known to be relatively unstable. Consequently, any purification by column chromatography was undertaken after pre-treating the column with 3% Et$_3$N/hexane solution, and the isolated pure compounds were stored at −20° C.

Synthesis of the Aminothiophene.

2-Bromothiophene (0.30 mL, 3.07 mmol, CAS 1003-09-4), copper(I) iodide (87 mg, 15 mol %), copper powder (30 mg, 15 mol %, CAS 7440-50-8), potassium phosphate tribasic (1.30 g, 24.6 mmol), were suspended in 2-(benzylamino)ethanol (4 mL) and heated at 80° C. for 20 h under Ar. After this time, the reaction mixture was allowed to cool to room temperature and water (10 mL) added. The solution was extracted with diethyl ether (3×10 mL), and the combined organic fractions washed with brine (1×20 mL), dried over MgSO$_4$ and the solvent removed in vacuo. Purification was undertaken by silica gel column chromatography (column loaded using 3% Et$_3$N/hexane) using 3:1 hexane/ethyl acetate to elute the product as an orange oil (207 mg, 0.89 mmol, 29%).

Modification of Aminothiophene.

To a solution of 2-[benzyl(thiophen-2-yl)amino]ethanol (163 mg, 0.70 mmol) and propargyl chloride (0.18 mL, 2.51 mmol) in toluene (3 mL) was added a solution of tetrabutylammonium bisulfate (30 mg) in 50% sodium hydroxide solution (3 mL) and the reaction mixture was stirred at room temperature for 3 days. The organic layer was separated and the solvent removed in vacuo. The resulting residue was dissolved in CHCl$_3$ (15 mL), washed with water (2×10 mL), dried over MgSO$_4$ and the solvent removed in vacuo. Purification was undertaken by silica gel column chromatography (column loaded using 3% Et$_3$N/hexane) using 5% ethyl acetate/hexane to elute the product as an off-white solid (68 mg, 0.25 mmol, 36%).

Formation of Croconaine Compound.

Croconic acid (18 mg, 0.13 mmol, CAS 488-86-8) and N-benzyl-N-[2-(prop-2-yn-1-yloxy)ethyl]thiophen-2-amine (68 mg, 0.25 mmol) were dissolved in 1:1 anhydrous toluene/1-butanol (4 mL) and heated at reflux for 1 h under Ar. After this time, the solution was allowed to cool to room temperature and the solvent removed in vacuo. The crude residue was purified by silica gel column chromatography using 2.5% MeOH/DCM to elute the product as a black solid (64 mg, 0.10 mmol, 79%).

Compound 2 has the same ability as compound 1 to increase the temperature of a solution. A 0.6 mL solution of compound 2 in 4:1 MeOH/H$_2$O at 2.0 or 50.0 μg/mL was stirred using a magnetic stirrer bar in a 1 cm Helma cuvette located in an air-conditioned room maintained at 295 K. An Omega hypodermic thermocouple (HYPO-33-1-T-G-60-SMPW-M) was placed in the solution and the temperature measured using the associated USB converter. The Ti:Sapphire laser beam was aligned to pass through the solution (above the stirrer and avoiding close contact with the thermocouple) in an identical manner in every experiment. The laser wavelength was set at 780 or 808 nm and the power controlled to be 250 mW during all of the experiments, with a beam diameter of 0.3 cm. Hence, the laser power density was 3.5 W/cm$^2$.

Example 6

Synthesis of Compound 3

Figure 4:
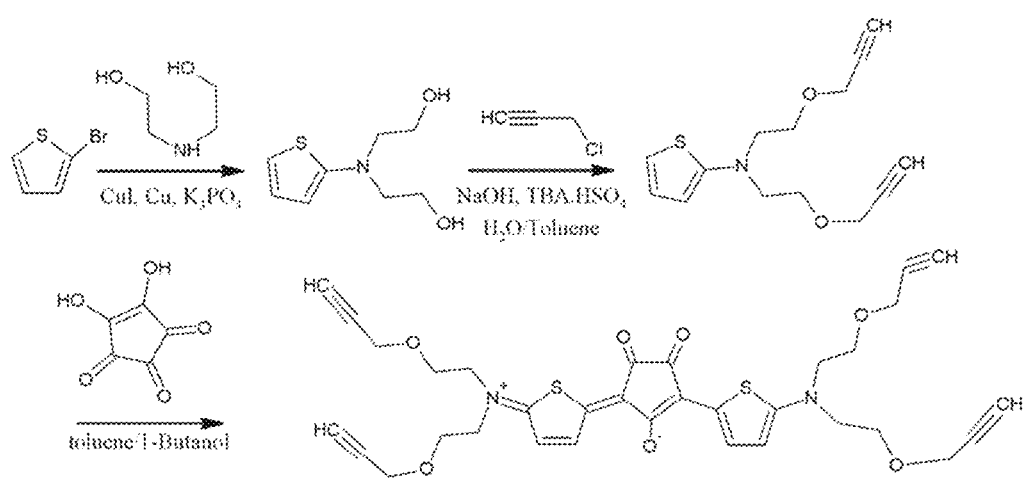
FIG. 4 depicts a scheme of synthesis of compound (3).

This example describes the synthesis of compound 3. With reference to FIG. 4:

Commercially available solvents and chemicals were used without further purification unless otherwise stated. Such materials can be procured from material supplies such as Sigma-Aldrich, Alfa Aesar, VWR, Fisher, Fluka, Acro Organics, and/or other suppliers, as may be required and/or desired in a particular embodiment. Water was de-ionized and microtiltered. Cu(I)TBTA.Br was synthesized from CuBr and TBTA, and stored in a desiccator prior to use. Aminothiophenes are known to be relatively unstable. Consequently, any purification by column chromatography was undertaken after pre-treating the column with 3% Et$_3$N/hexane solution, and the isolated pure compounds were stored at −20° C.

Synthesis of the Aminothiophene.

2-Bromothiophene (1.19 mL, 12.3 mmol, CAS 1003-09-4), copper(I) iodide (350 mg, 15 mol %), copper powder (117 mg, 15 mol %, CAS 7440-50-8), potassium phosphate tribasic monohydrate (5.65 g, 24.5 mmol), were suspended in diethanolamine (12 mL) and heated at 80° C. for 20 h under Ar. After this time, the reaction mixture was allowed to cool to room temperature and water (40 mL) added. The solution was extracted with diethyl ether (3×40 mL), and the combined organic fractions washed with brine (1×60 mL), dried over MgSO$_4$ and the solvent removed in vacuo. Purification was undertaken by silica gel column chromatography (column loaded and pretreated using 3% Et$_3$N/hexane) using 4:1 ethyl acetate/hexane to elute the product as an orange oil (538 mg, 2.87 mmol, 23%).

Modification of Aminothiophene.

To a solution of 2,2'-(thiophen-2-ylazanediyl)bis(ethan-1-ol) (336 mg, 2.86 mmol) and propargyl chloride (1.14 mL, 10.3 mmol) in toluene (15 mL) was added a solution of tetrabutylammonium bisulfate (100 mg) in 50% sodium hydroxide solution (10 mL) and the reaction mixture was stirred at room temperature for 3 days. The organic layer was separated and the solvent removed in vacuo. The resulting residue was dissolved in $CHCl_3$ (50 mL), washed with water (2×20 mL), dried over $MgSO_4$ and the solvent removed in vacuo. Purification was undertaken by silica gel column chromatography (column loaded and pretreated using 3% $Et_3N$/hexane) 4:1 hexane/ethyl acetate to elute the product as an off-white solid (378 mg, 1.44 mmol, 50%).

Formation of Croconaine Compound.

Croconic acid (27 mg, 0.19 mmol, CAS 488-86-8) and N,N-bis(2-(prop-2-yn-1-yloxy)ethyl)thiophen-2-amine (100 mg, 0.38 mmol) were dissolved in 1:1 anhydrous toluene/1-butanol (8 mL) and heated at reflux for 1 h under Ar. After this time, the solution was allowed to cool to room temperature and the solvent removed in vacuo. The crude residue was purified by silica gel column chromatography using 2% MeOH/DCM to elute the product as a black solid (84 mg, 0.13 mmol, 70%).

Example 7

Synthesis of Compound 4

Figure 5:
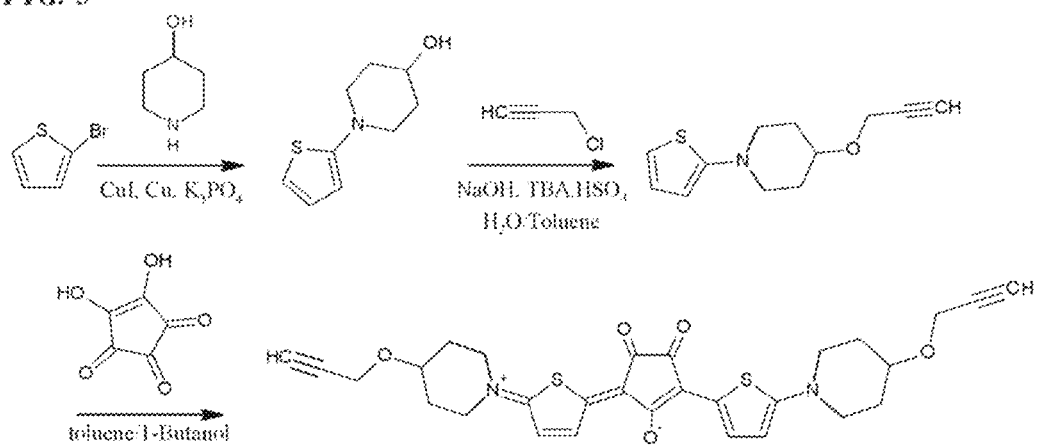
FIG. 5 depicts a scheme of synthesis of compound (4).

This example describes the synthesis of compound 4. With reference to FIG. 5:

Commercially available solvents and chemicals were used without further purification unless otherwise stated. Such materials can be procured from material supplies such as Sigma-Aldrich, Alfa Aesar, VWR, Fisher, Fluka, Acro Organics, and/or other suppliers, as may be required and/or desired in a particular embodiment. Water was de-ionized and microfiltered. Cu(I)TBTA.Br was synthesized from CuBr and TBTA, and stored in a desiccator prior to use. Aminothiophenes are known to be relatively unstable. Consequently, any purification by column chromatography was undertaken after pre-treating the column with 3% $Et_3N$/hexane solution, and the isolated pure compounds were stored at −20° C.

Synthesis of the Aminothiophene.

2-Bromothiophene (1.19 mL, 12.3 mmol, CAS 1003-09-4), 4-hydroxypiperidine (1.62 g, 16.0 mmol), copper(I) iodide (350 mg, 15 mol %), copper powder (117 mg, 15 mol %, CAS 7440-50-8) and potassium phosphate tribasic (5.22 g, 24.6 mmol) were suspended in 2-dimethylaminoethanol (12 mL) and heated at 80° C. for 20 h under Ar. After this time, the reaction mixture was allowed to cool to room temperature and water (40 mL) added. The solution was extracted with diethyl ether (3×40 mL), and the combined organic fractions washed with brine (1×60 mL), dried over MgSO4 and the solvent removed in vacuo. Purification was undertaken by silica gel column chromatography (column loaded and pre-treated with 3% Et3N/hexane) using 7:3 hexane/ethyl acetate to elute the product as an off-white oil (1.25 g, 6.82 mmol, 56%).

Modification of Aminothiophene.

To a solution of 1-(thiophen-2-yl)piperidin-4-ol (2) (400 mg, 2.18 mmol) and propargyl chloride (0.77 mL, 10.6 mmol) in toluene (15 mL) was added a solution of tetrabutylammonium bisulfate (74 mg) in 50% sodium hydroxide solution (10 mL) and the reaction mixture was stirred at room temperature for 7 days. The organic layer was separated and the solvent removed in vacuo. The resulting residue was dissolved in $CHCl_3$ (50 mL), washed with water (2×25 mL), dried over $MgSO_4$ and the solvent removed in vacuo. Purification was undertaken by silica gel column chromatography (column loaded and pre-treated with 3% $Et_3N$/hexane) using 3% ethyl acetate/hexane to elute the product as an off-white solid (238 mg, 1.08 mmol, 50%).

Formation of Croconaine Compound.

Croconic acid (74 mg, 0.52 mmol, CAS 488-86-8) and 4-(prop-2-yn-1-yloxy)-1-(thiophen-2-yl)piperidine (5) (231 mg, 1.04 mmol) were dissolved in 1:1 anhydrous toluene/1-butanol (20 mL) and heated at reflux for 90 min. After this time, the solution was allowed to cool to room temperature and the solvent removed in vacuo. The crude residue was purified by silica gel column chromatography using 3% MeOH/DCM to elute the product as a black solid (131 mg, 0.24 mmol, 46%).

Example 8

Preparation of Croconaine-Containing Nanoparticles

This example describes a method of synthesizing nanoparticles containing croconaine compound. Star polymer (5.0 mg, $1.7 \times 10^{-10}$ mol) and compound 1 (0.50 mg, 0.95 mmol) were dissolved in THF (1.5 mL) and stirred for 24 h. After this time, water (1.5 mL) was added and the mixture stirred for a further 24 h. The solvent was removed in vacuo, water (2 mL) added, and the suspension sonicated for 10 minutes. Undissolved compound was removed by centrifugation and the precipitate washed with water (3×1 mL).

Figure 6:
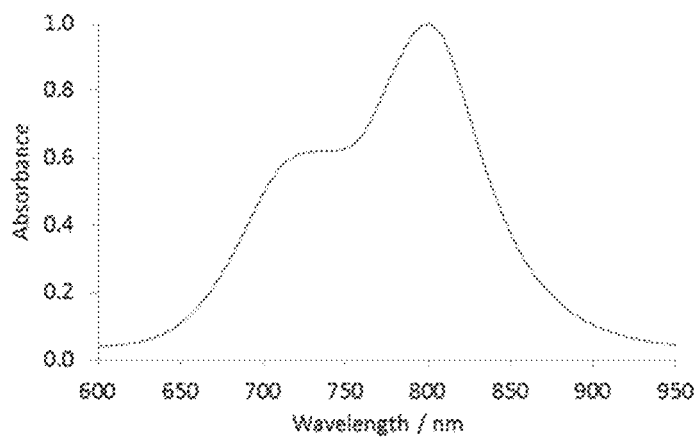
FIG. 6 depicts the normalized absorption spectrum of croconaine containing star polymer ($H_2O$).

The absorption spectrum of the combined supernatant and filtrate indicated successful compound-encapsulation within the star polymer particles (FIG. 6), while absorption analysis of the recovered compound compared to a known control sample gave a loading estimate of 55-60%. Hence, approximately 3100 croconaine molecules have been encapsulated per nanoparticle.

Example 9

Destroying Human Cancer Cells

This example describes a method of use of a photothermal croconaine compounds to destroy human cancer cells. Nanoparticles containing croconaine compound are prepared as presented in Example 8 above.

Human cancer cells are cultured in a 96-well microplate and grown to 80% confluency. Cells are incubated with nanoparticles containing croconaine compound and then exposed to the diode laser light (5 min, 2 $W/cm^2$). After treatment, cells are incubated with Calcein AM (5 Ag/mL in culture medium; 1 h incubation), a fluorescent indicator of esterase activity in viable cells, and imaged using phase and fluorescence microscopy.

Example 10

Destroying Tumors in Mice

This example describes a method of use of a photothermal croconaine compounds to destroy tumors in mice. Nanoparticles containing croconaine compound are prepared as presented in Example 8 above.

Xenografted tumors are established by subcutaneously injecting cancer cells into the left flank of 4-5 week-old nude mice. Tumor size is measured periodically using calipers and the tumors allowed to grow to 7-8 mm in diameter. The experimental tumor-bearing nude mouse is then intravenously injected with 200 mL nanoparticles containing croconaine compound, at a concentration of 2 mg/mL via tail vein, while the control tumor-bearing nude mouse is intravenously injected with 200 mL PBS (pH 7.4). The tumors are irradiated with near infrared laser light at an output power of 20 W/cm2 for 30 min after 4 h post-injection of nanoparticles. The surface temperature of the tumor under near infrared laser irradiation gradually increases to 42-47° C. within 30 min, which is suitable temperature to kill tumor cells in vivo, while the healthy tissue near the tumor does not show significant temperature change. Two days later, mice are again subjected to near infrared light irradiation for 30 min after 4 h post-injection of nanoparticles. The body weight and tumor size are measured three times per week. The tumor volume is calculated.

Example 11

Photoacoustic Imaging of Tumors in Mice

This example describes a method of use of a photothermal croconaine compounds to image tumors in mice. Nanoparticles containing croconaine compound are prepared as presented in Example 8 above.

Cancer cells are subcutaneously injected into the left flank of 4-5 week-old nude mice. Tumor size is measured periodically using calipers and the tumors allowed to grow to 7-8 mm in diameter. The experimental tumor-bearing nude mouse is then intravenously injected with 200 mL nanoparticles containing croconaine compound, at a concentration of 2 mg/mL via tail vein, while the control tumor-bearing nude mouse is intravenously injected with 200 mL PBS (pH 7.4). The mice are anesthetized and placed in the supine position in the animal holder. Cross-sectional multispectral optoacoustic image datasets are acquired through the tumor at 6 different wavelengths in the NIR-window (700 nm, 740 nm, 760 nm, 780 nm, 800 nm, 900 nm). Reconstruction of single-wavelength optoacoustic images is done with interpolated matrix model inversion (IMMI) method.

Example 12

Tissue Welding Using Rats

This example describes a method of use of a photothermal croconaine compounds to secure closed an incision. Nanoparticles containing croconaine compound are prepared as presented in Example 8 above.

Rats are anesthetized with isoflourane and their backs shaved. The shaved area is swabbed with chlorhexadine gluconate solution and draped. Two full-thickness incisions 4-5 cm long are made on the backs of each animal. The incision on the animal's left is closed with interrupted polypropylene 5-10 sutures (PROLENE, Ethicon) at a spacing of approximately 3 mm, while the other incision is closed by welding using the nanoparticle solder formulation of croconaine containing nanoparticles mixed with bovine serum albumin. Approximately 10-15 ml of solder is applied with a spatula to both sides of the wound, coating the full depth of the incision. The skin is brought into contact with tweezers and then welding is accomplished using the 808 nm laser at an output of 14 W/cm² and a 5 mm spot size at an angle from the skin between 45 and 60°. The laser is scanned across the incision site at a rate of 1 mm/second.

What is claimed is:

1. A compound of formula (I):

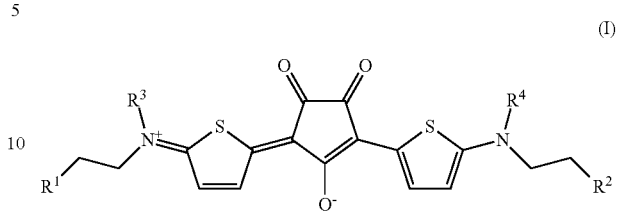

wherein:
R¹ and R² are the same and are selected from selected from the group consisting of heteroaryl, alkoxy, aryloxy, and a first reactive group; and R³ and R⁴ are the same and are selected from the group consisting of —H, alkyl, substituted alkyl, arylalkyl, aryl, substituted aryl, heteroaryl, and a second reactive group;

wherein the first reactive group and the second reactive group are each independently

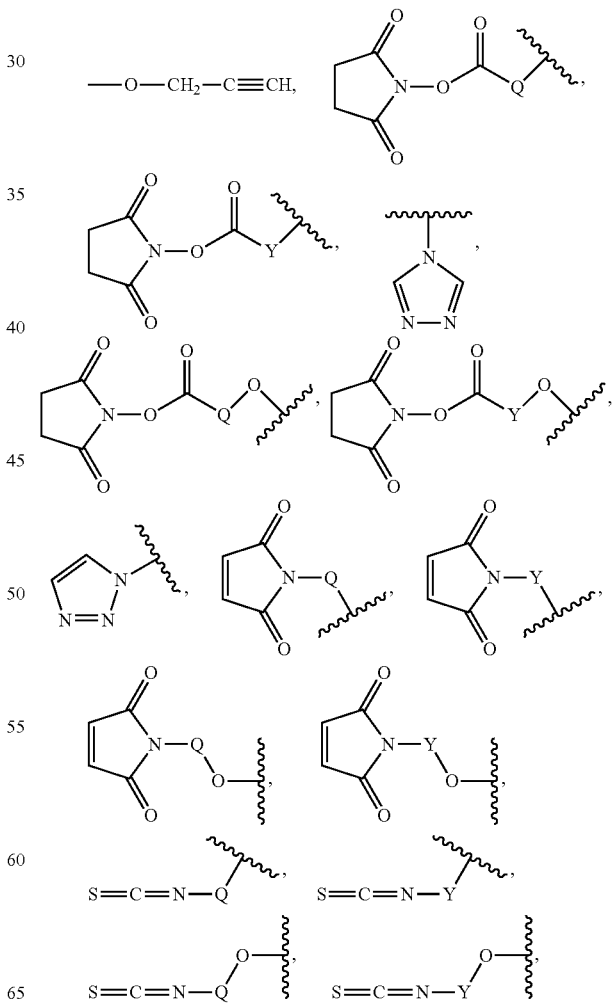

-continued

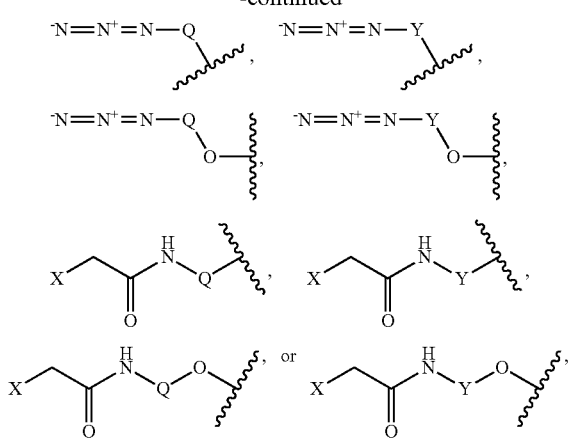

wherein Q is alkyl, Y is aryl, X is halo, and the wavy line indicates the point of attachment to $R^1$, $R^2$, $R^3$ or $R^4$;
or wherein $R^1$ and $R^3$ taken together form a substituted 5- or 6-membered ring, wherein the ring is substituted with a first reactive group;

or wherein $R^2$ and $R^4$ taken together form a substituted 5- or 6-membered ring, wherein the ring is substituted with a first reactive group, and when $R^1$ and $R^3$ taken together form a substituted 5- or 6-membered ring, $R^2$ and $R^4$ are taken together form a substituted 5- or 6-membered ring, and $R^1$ and $R^3$ taken together and $R^2$ and $R^4$ taken together are the same;

or a pharmaceutically acceptable salt, optical isomer, geometric isomer or tautomer thereof.

2. The compound of claim 1, wherein said first reactive group is —O—CH$_2$—C≡CH.

3. The compound of claim 2, wherein said second reactive group is —O—CH$_2$—C≡CH.

4. A compound selected from the group consisting of:

compound (1)

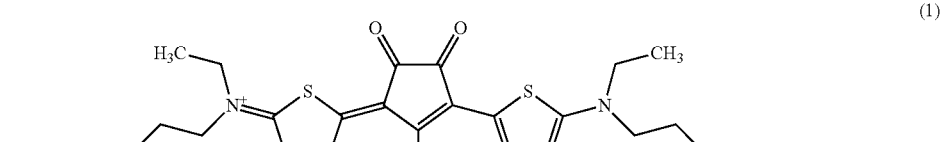

(1)

compound (2)

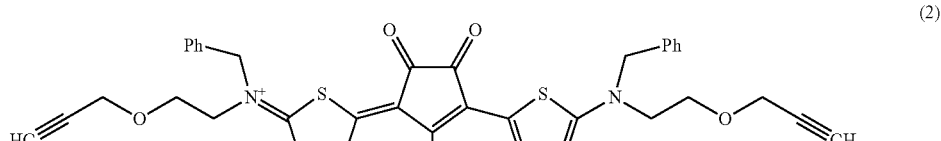

(2)

compound (3)

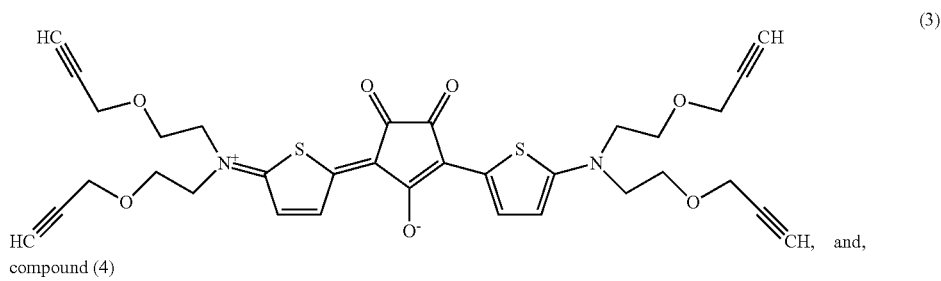

(3)

compound (4)

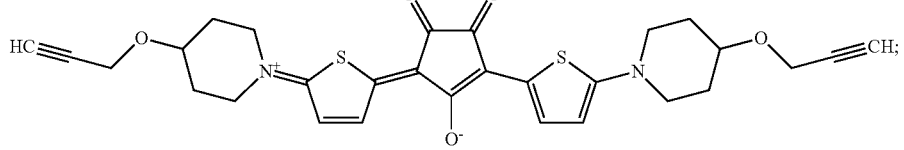

(4)

or a pharmaceutically acceptable salt, optical isomer, geometric isomer or tautomer thereof.

5. The compound of claim 1 wherein $R^1$ is a first reactive group or tetrazole.

6. The compound of claim 5 wherein the first reactive group is —O—CH$_2$—C≡CH.

7. The compound of claim 5 wherein R$^2$ is a first reactive group or tetrazole.

8. The compound of claim 7; wherein the first reactive group is —O—CH$_2$—C≡CH.

9. The compound of claim 1 wherein R$^1$ and R$^2$ are both reactive groups.

10. The compound of claim 1 wherein R$^3$ and R$^4$ are both ethyl, benzyl, or second reactive groups.

11. The compound of claim 1 wherein the compound of formula (I) is compound (1):

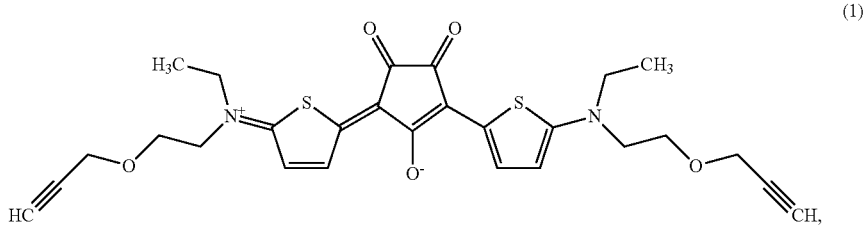 [SMILES: C#CCOCCN(CC)c1ccc(C2=C([O-])/C(=C3C=C/C(=[N+](/CC)CCOCC#C)S\3)C(=O)C2=O)s1]

or a pharmaceutically acceptable salt, geometric isomer, or tautomer thereof.

12. A process of making a compound of formula (I):

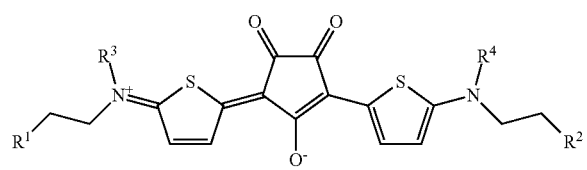

wherein:
R$^1$ and R$^2$ are the same and are selected from the group consisting of —H, alkyl, substituted alkyl, arylalkyl, aryl, substituted aryl, heteroaryl, substituted heteroaryl, carboxylic acid, alkoxy, aryloxy, amino, dialkylamino, triazole, alkyl hydroxysuccinimide ester, alkyl maleimide, alkyl isothiocyanate, alkyl azide, alkyl alkyne, alkyl haloacetamido, aryl ester, aryl hydroxysuccinimide ester, aryl maleimide, aryl isothiocyanate, aryl azide, aryl alkyne, aryl haloacetamido, alkoxy hydroxysuccinimide ester, alkoxy maleimide, alkoxy isothiocyanate, alkoxy azide, —O—CH$_2$—C≡CH, alkoxy haloacetamido, aryloxy ester, aryloxy hydroxysuccinimide ester, aryloxy maleimide, aryloxy isothiocyanate, aryloxy azide, aryloxy alkyne, and aryloxy haloacetamido;

R$^3$ and R$^4$ are the same and are selected from the group consisting of —H, alkyl, substituted alkyl, arylalkyl, aryl, substituted aryl, heteroaryl, substituted heteroaryl, carboxylic acid, alkyl hydroxysuccinimide ester, alkyl maleimide, alkyl isothiocyanate, alkyl azide, alkyl alkyne, alkyl haloacetamido, aryl ester, aryl hyroxysuccinimide ester, aryl maleimide, aryl isothiocyanate, aryl azide, aryl alkyne, and aryl haloacetamido;

or wherein R$^1$ and R$^3$ taken together form an optionally substituted 5- or 6-membered ring;

or wherein R$^2$ and R$^4$ taken together form an optionally substituted 5- or 6-membered ring;

or a pharmaceutically acceptable salt, optical isomer, geometric isomer or tautomers thereof, comprising contacting croconic acid with a compound of formula (II),

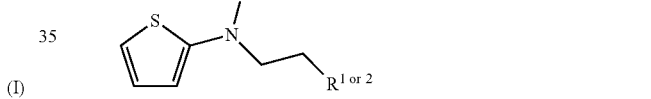

under conditions suitable for producing the photothermal compound of formula (I), wherein:
R$^1$, R$^2$, R$^3$, and R$^4$ are as defined for formula (I).

13. The process as in claim 12, wherein said conditions suitable for producing the croconaine compound include heating to 120-130° C.

14. The process as in claim 12, wherein said conditions suitable for producing the croconaine compound include heating for 45-75 minutes.

15. The process as in claim 12, further comprising the steps of contacting a compound of formula (III),

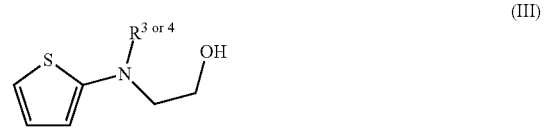

wherein:
R$^3$ and R$^4$ are each independently selected from the group consisting of —H, alkyl, substituted alkyl, arylalkyl, aryl, substituted aryl, heteroaryl, substituted heteroaryl, carboxylic acid, alkyl hydroxysuccinimide ester, alkyl maleimide, alkyl isothiocyanate, alkyl azide, alkyl alkyne, alkyl haloacetamido, aryl ester, aryl hydroxysuccinimide ester, aryl maleimide, aryl isothiocyanate, aryl azide, aryl alkyne, and aryl haloacetamido;

with a compound of formula (IV),

 (IV)

wherein:

R¹ and R² are each independently selected from the group consisting of —H, alkyl, substituted alkyl, arylalkyl, aryl, substituted aryl, heteroaryl, substituted heteroaryl, carboxylic acid, alkoxy, aryloxy, amino, dialkylamino, triazole, alkyl hydroxysuccinimide ester, alkyl maleimide, alkyl isothiocyanate, alkyl azide, alkyl alkyne, alkyl haloacetamido, aryl ester, aryl hydroxysuccinimide ester, aryl maleimide, aryl isothiocyanate, aryl azide, aryl alkyne, aryl haloacetamido, alkoxy hydroxysuccinimide ester, alkoxy maleimide, alkoxy isothiocyanate, alkoxy azide, alkoxy alkyne, alkoxy haloacetamido, aryloxy ester, aryloxy hydroxysuccinimide ester, aryloxy maleimide, aryloxy isothiocyanate, aryloxy azide, aryloxy alkyne, and aryloxy haloacetamido;

under conditions suitable to form a compound of formula (II),

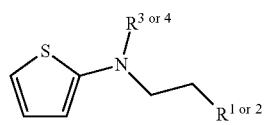 (II)

wherein:
R¹, R², R³, and R⁴ are defined for formulas (III) and (IV).

16. The process as in claim 15, wherein the conditions suitable to form a compound of formula (II) include stirring at room temperature for 24-48 hours.

17. The process as in claim 15, further comprising the steps characterized by contacting a compound of formula (V),

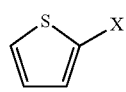 (V)

wherein:
X is a halogen atom,
with a compound of formula (VI),

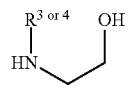 (VI)

wherein:

R³, and R⁴ are each independently selected from the group consisting of —H, alkyl, substituted alkyl, arylalkyl, aryl, substituted aryl, heteroaryl, substituted heteroaryl, carboxylic acid, alkyl hydroxysuccinimide ester, alkyl maleimide, alkyl isothiocyanate, alkyl azide, alkyl alkyne, alkyl haloacetamido, aryl ester, aryl hydroxysuccinimide ester, aryl maleimide, aryl isothiocyanate, aryl azide, aryl alkyne, and aryl haloacetamido;

or a pharmaceutically acceptable salt, optical isomer, geometric isomer and/or tautomers thereof, under conditions suitable to form a compound of formula (III),

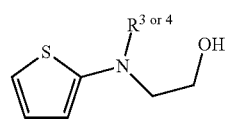 (III)

wherein:
R³, and R⁴ are as defined for formula (VI).

18. The process as in claim 17, wherein said conditions suitable to form a compound of formula (III) include heating to 70-90° C.

19. The process as in claim 17, wherein said conditions suitable to form a compound of formula (III) include heating for 15-25 hours.

20. A process of making a croconaine compound of formula (1),

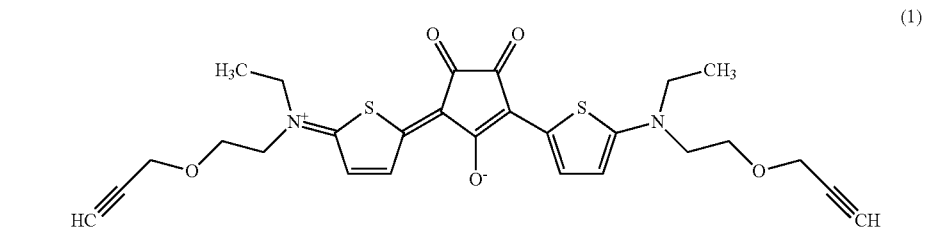 [SMILES: C#CCOCCN(CC)c1ccc(C2=C([O-])/C(=C3C=C/C(=[N+](/CC)CCOCC#C)S\3)C(=O)C2=O)s1] (1)

comprising contacting 2-bromothiophene with 2-(ethylamino)ethanol in a solvent, in the presence of copper(I) iodide, copper powder, and potassium phosphate tribasic, under reflux conditions, forming an aminothiophene of formula (10),

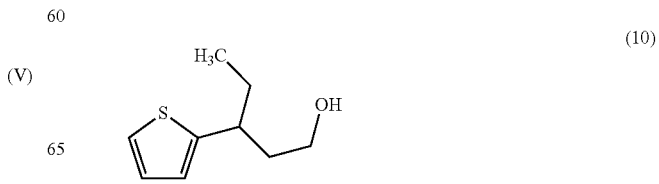 (10)

contacting said aminothiophene with propargyl chloride in a solvent, forming a modified aminothiophene of formula (12),
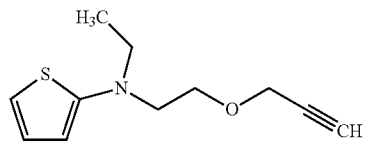
(12)
contacting said modified aminothiophene with croconic acid, in solvent, under reflux conditions, forming said croconaine compound.